United States Patent [19]

Huttllin

[11] Patent Number: 5,147,593
[45] Date of Patent: Sep. 15, 1992

[54] METHOD TO PREPARE EXTRUDED PARTICLES BY BREAKING WITH AN AIR STREAM

[76] Inventor: Herbert Huttllin, Daimlerstrasse 7, 7853 Steinen, Fed. Rep. of Germany

[21] Appl. No.: 611,971

[22] Filed: Nov. 8, 1990

[30] Foreign Application Priority Data

Oct. 1, 1990 [DE] Fed. Rep. of Germany ....... 4000571

[51] Int. Cl.$^5$ .............................................. B29C 9/02
[52] U.S. Cl. .................... 264/500; 264/142; 264/143
[58] Field of Search ................... 264/12, 13, 142, 143, 264/148, 500, 14, 121, 504; 425/72.2, 289, 308, 72.1

[56] References Cited

U.S. PATENT DOCUMENTS

| | | | |
|---|---|---|---|
| 3,213,170 | 10/1965 | Erdmenger et al. | 264/142 |
| 3,759,642 | 9/1973 | Poteef | 425/289 |
| 3,846,529 | 11/1974 | Poteef | 425/289 |
| 3,959,421 | 5/1976 | Weber et al. | 264/14 |
| 4,102,662 | 7/1978 | Levecque et al. | 264/12 |
| 4,151,251 | 4/1979 | Kropa | 264/142 |
| 4,582,473 | 4/1986 | Rizzi et al. | 425/225 |
| 4,954,352 | 9/1990 | Luker | 264/142 |
| 4,960,547 | 10/1990 | Reinhard | 425/289 |
| 4,966,737 | 10/1990 | Werner et al. | 264/14 |

FOREIGN PATENT DOCUMENTS

| | | | |
|---|---|---|---|
| 2200114 | 7/1973 | Fed. Rep. of Germany . | |
| 47-1542 | 1/1972 | Japan | 425/289 |
| 56-142014 | 11/1981 | Japan | 264/142 |
| 1-247112 | 3/1989 | Japan . | |
| 1108972 | 4/1968 | United Kingdom . | |
| 1298121 | 11/1972 | United Kingdom . | |

*Primary Examiner*—Jay H. Woo
*Assistant Examiner*—Robert B. Davis
*Attorney, Agent, or Firm*—Brumbaugh, Graves, Donohue & Raymond

[57] ABSTRACT

Extruded particles (H), especially as a precursor for pharmaceutical pellets are prepared by extruding a doughy mass in the form of a strand (G) into a gas stream (E) in which it is predried and also broken by the gas stream (E). A lance (40) is employed for the extrusion which extends through a treatment chamber (12) and carries extruder nozzles (80) opening transversely of the general flow of gas (E). A pressure gas nozzle (96) fed intermittently with pressurized air is directed to the opening range of each extruder nozzle (80).

6 Claims, 7 Drawing Sheets

METHOD TO PREPARE EXTRUDED PARTICLES BY BREAKING WITH AN AIR STREAM

The invention relates to a method of preparing extruded particles, especially as a precursor for pharmaceutical pellets, wherein a doughy mass in the form of a strand is extruded into a gas stream transversely of the same and broken by the gas stream. The invention further relates to an apparatus for carrying out such a method, comprising at least one treatment chamber which has at least one gas inlet and at least one gas outlet to generate a general flow of gas in the treatment chamber, and at least one pump to convey a mass for extrusion through extruder nozzles which open into the treatment chamber transversely of the general flow of gas.

A method and an apparatus of this kind are known from U.S. Pat. No. 3,213,170. In that case a doughy mass in the form of a strand is extruded horizontally into a passage in which a gas stream is guided vertically from top to bottom. The extruded particles are dried and sheared by the gas stream and then drop tangentially into a horizontal tube in which they are caused to move in rotation, thereby being rounded.

If the gas stream is adjusted to be strong with this known process so as to break off the extruded particles after the shortest possible time, that involves the risk of the extruded particles remaining moist at their leeward side so that they will agglomerate with other extruded particles upon dropping. If adjustment of the gas stream, on the other hand, is weak so that the extruded particles will dry uniformly, that involves the risk of the particles not breaking in time and becoming jammed in the passage.

It is, therefore, the object of the invention to improve a method of preparing extruded particles and to devise an apparatus for carrying out that method so that the risk of mutual adherence or jamming of the extruded particles is reliably avoided.

As regards the method, that object is met, in accordance with the invention, starting from a method as specified initially, in that predrying and the breaking of the strand are prepared by a general flow of gas and backed up by at least one sharply focussed pressure gas jet directed at the strand.

To carry out the method according to the invention, preferably an apparatus is used with which, according to the invention, at least one hollow lance extends transversely of the general flow of gas in the treatment chamber which lance comprises the extruder nozzles and includes a conveyor channel extending in longitudinal direction of the lance and communicating through a longitudinal slot with a distributor channel to which the extruder nozzles are connected.

An embodiment of an apparatus according to the invention will be described further with reference to the accompanying diagrammatic drawings, in which.

The fluidized bed apparatus illustrated comprises a housing 10 which presents a parallelepiped of elongated configuration in horizontal direction and has thermally insulated walls. Six treatment chambers 12 are formed inside the housing 10, having a common bottom 14, two gas inlets 16 each located in the bottom, and gas outlets 18 of which five each are associated with two adjacent treatment chambers 12.

Through the gas inlets 16, the treatment chambers 12 communicate with a common air supply chamber 20 disposed under the bottom 14 and receiving dehumidified hot air or another gas for treatment through connections 22. The gas outlets 18 open into spent air chambers 24 arranged at the longitudinal sides of the housing 10 and extending down to below the bottom 14 where they are adapted to be connected to the suction end of a conventional blower through connections 26. In operation, each treatment chamber 12 is closed at the top by a lid 28 made, for example, of glass and adapted to be swung open for cleaning purposes.

A conveyor belt 30 permeable to gas, such as a known articulated or jointed band of metal or plastics wire helices, lies on the bottom 14 and extends in longitudinal direction through the entire housing 10. The conveyor belt 30 may be withdrawn from a pay-off reel 32 and wound up, after use, on a take-up reel 34. Instead of these two reels 32 and 34, deflecting pulleys may be provided around which an endless conveyor belt is passed. The face ends at which the conveyor belt 30 enters into and leaves the housing 10 normally are closed by a flap 36 each.

Figure 1:
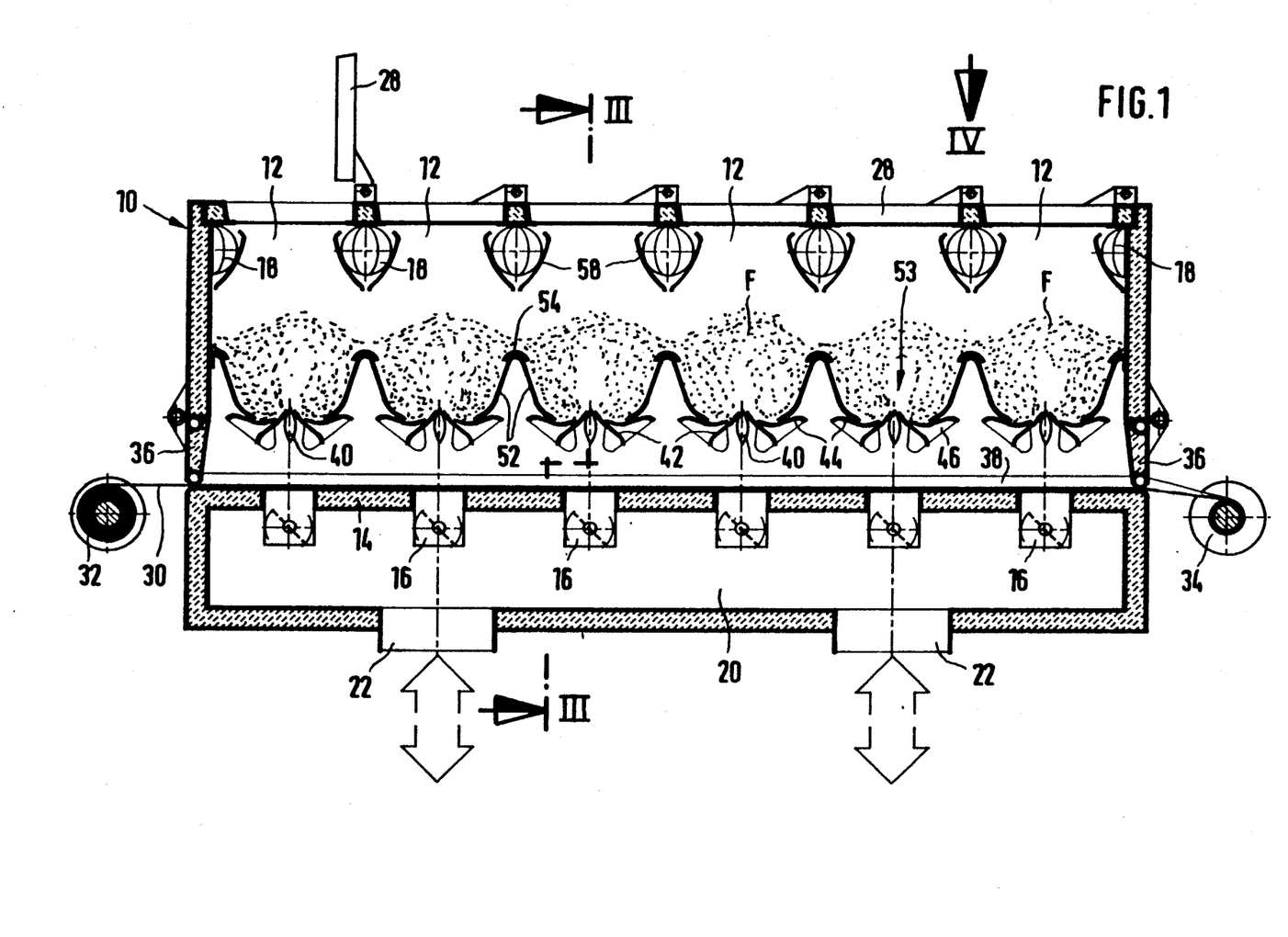
FIG. 1 is a longitudinal sectional elevation in the vertical plane I—I of FIG. 3 of an apparatus for preparing extruded particles of a doughy mass.

To empty the treatment chambers 12, it is provided to place a foil 38 on a section of the conveyor belt 30 which is somewhat longer than the housing 10. By moving the conveyor belt 30, this foil subsequently is brought into the housing 10, loaded with material made or processed in the treatment chambers 12, and then moved out of the housing 10 together with that material by renewed movement of the conveyor belt 30. As indicated in FIG. 1, the foil 38 is drawn upwardly to such an extent at the lateral limits of the treatment chambers 12 that any contamination of the conveyor belt 30 by the composition being produced and/or treated is avoided.

All the built-in structures which will be described below are symmetrical with respect to a vertical center plane A of the respective treatment chamber 12, which plane extends transversely of the longitudinal direction of the housing 10. A lance 40 passes horizontally and spaced above the bottom 14 through each treatment chamber 12 in the center plane A. The outline of each lance 40 is of drop shape, symmetrical with respect to the center plane A, being rounded at the bottom and pointed at the top. At both sides of this contour there are two guide vanes 42 and 44 each, disposed in parallel with the corresponding lance 40.

The two guide vanes 42 and 44 at one and the other side of the lance 40 are interconnected by plates 46, each extending in a vertical longitudinal plane and fastened on a shaft 48 which extends parallel to the lance 40. The shafts 48 are connected to a pivot drive means 50 each, for example an hydraulic or pneumatic rotary wing motor by means of which the associated guide vanes 42 and 44 are pivotable back and forth through an angular range of 30°, for instance.

Figure 5:
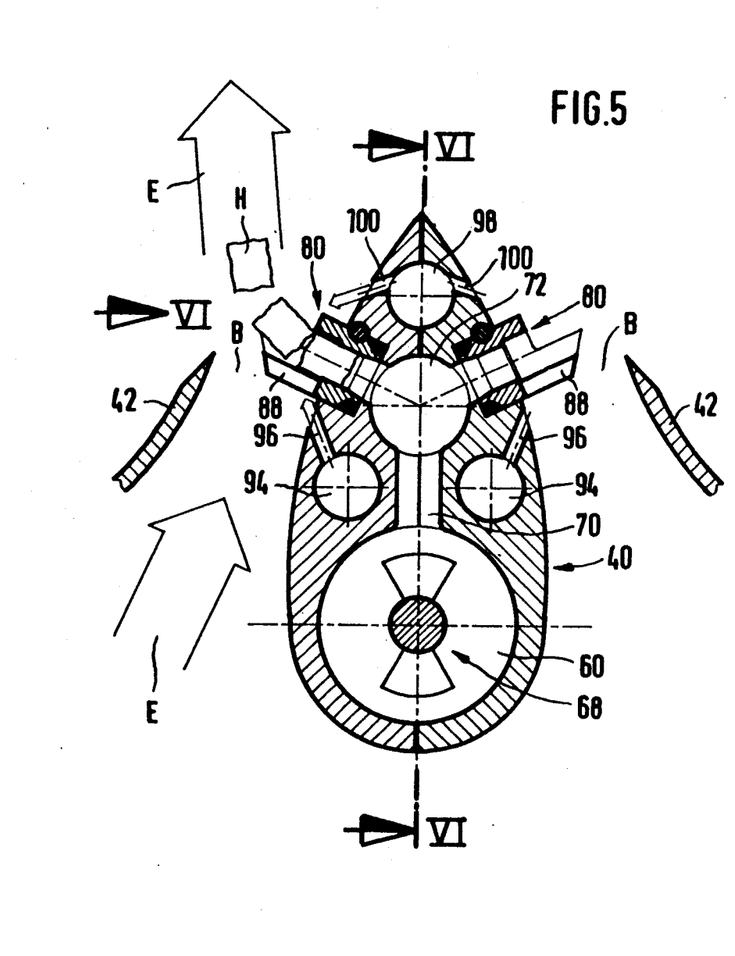
FIG. 5 is a much enlarged cutout of FIG. 2.
Figure 6:
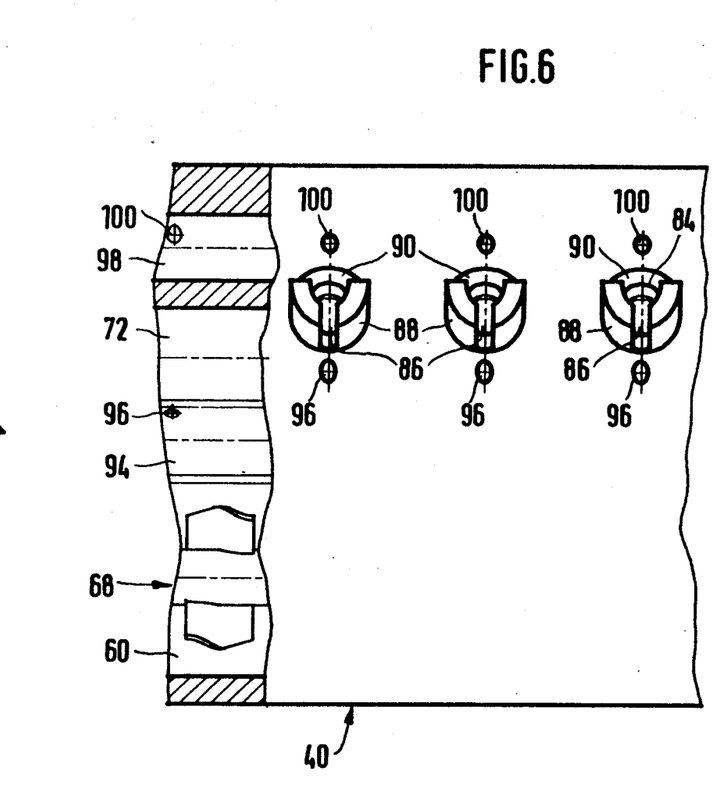
FIG. 6 is the corresponding side elevational view, shown partly as sectional view VI—VI of FIG. 5.

A semishell 52 each is arranged at either side of the lance 40, likewise extending parallel to the same. Together with the corresponding guide vanes 42 and 44 and the lance 40, the semishells 52 form a trough 53 which is almost totally closed at the bottom when the guide vanes are in their operating position—cf. second and third treatment chambers 12 from the right in FIG. 2—but leaves open three gaps B, C, and D at either side of the lance 40. These gaps extend throughout the width of the treatment chamber 12. Air used in the treatment, in the form a general flow of gas E (cf. FIGS. 5, 7 and 9) may flow through these gaps B, C, and D, starting from the corresponding gas inlets 16 and flowing around the lance 40 in upward direction, forming a fluidized bed F which is defined by the trough 53 (cf.FIG. 1 and second chamber from the right in FIG. 2).

Figure 2:
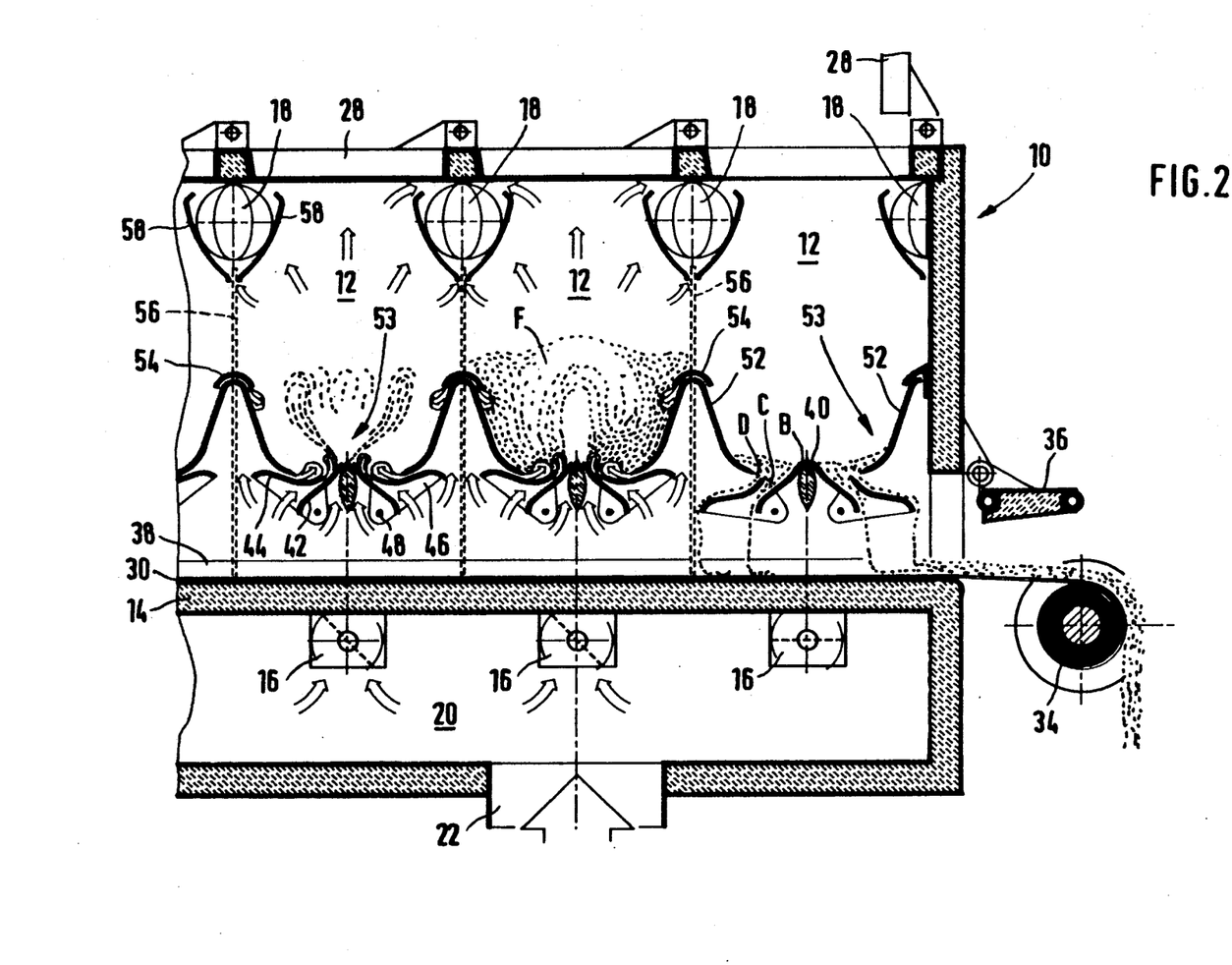
FIG. 2 is an enlarged cutout of FIG. 1.
Figure 3:
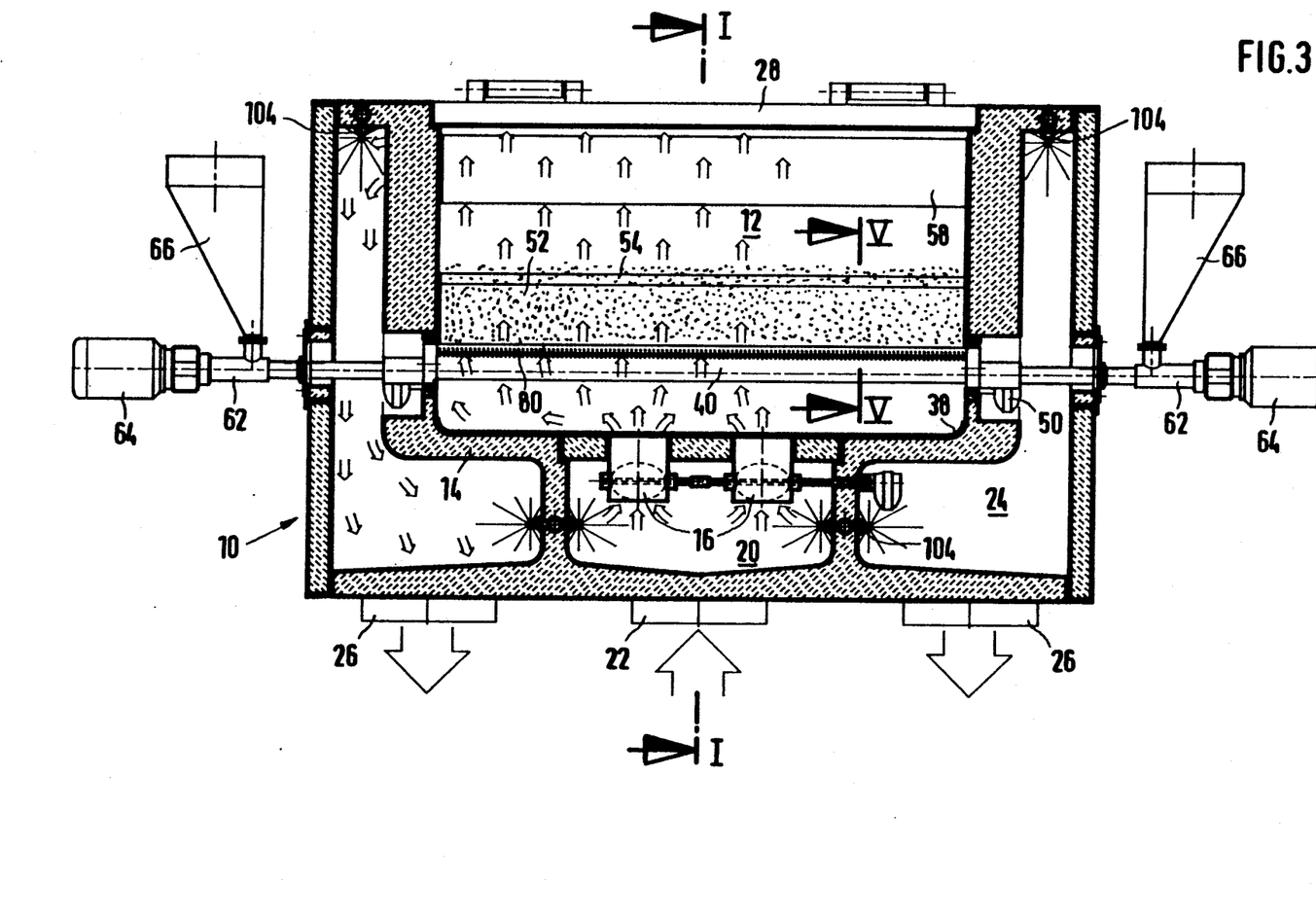
FIG. 3 is the vertical cross section III—III of FIG. 1.

The guide vanes 42 and 44 can be pivoted by the pivot drive means 50 from their operating position into an emptying position—cf. first chamber from the right in FIG. 2. In this position, the material which has accumulated in the trough 53 after shutdown of the air flow may trickle down through the gaps B, C, and D on to the foil 38.

An intermediate space is left free between the upper edges of the semishells 52 in adjacent treatment chambers 12, and this space is covered by a roof element or shaped cover 54 which is concave when looked at from below. Between the upper edge of each semishell 52 and the corresponding shaped cover 54 a gap D' is left open through which another part of the general flow of gas E flows from top to bottom into the respective trough 53. The shaped covers 54 are mounted in such a way that material may flow across them if it exceeds a certain level in one of the troughs 53. As an alternative, adjacent troughs 53 may be separated by a partition 56. The gas outlets 18 located at a higher level are covered by baffle plates 58 so that dustlike particles, at best, of the composition will get into the spent air chambers 24 where they can be separated in known manner from the gas stream by filtering.

Each lance 40 includes a conveyor channel 60 of circular cross section oriented in longitudinal direction and being disposed coaxially with the lower part of the lance profile likewise of circular arc shape, extending approximately for the full width of the housing 10. A pump 62 each is connected laterally to the ends of the conveyor channel 60. This may be a conventional eccentric worm type pump driven by an electric motor 64 and pressing a doughy mass for extrusion from a receptacle 66 into the conveyor channel 60. The rotor of each of the two pumps 62 is coupled to an agitator 68 extending in the conveyor channel 60 up to a central area of the corresponding lance 40 and making sure that the composition inside the conveyor channel 60 is stirred constantly and does not solidify.

The conveyor channel 60 communicates through a longitudinal slot 70 with a distributor channel 72 which likewise extends in longitudinal direction of the lance 40 and from which equally spaced bores 74 pass in oblique upward direction to the surface of the lance 40. The bores 74 each have a shoulder 76 where they are widened outwardly and where a sealing ring 78 is seated. An extruder nozzle 80 each is pushed into the enlarged outer region of each of the bores 74 up to the shoulder 76.

Figure 7:
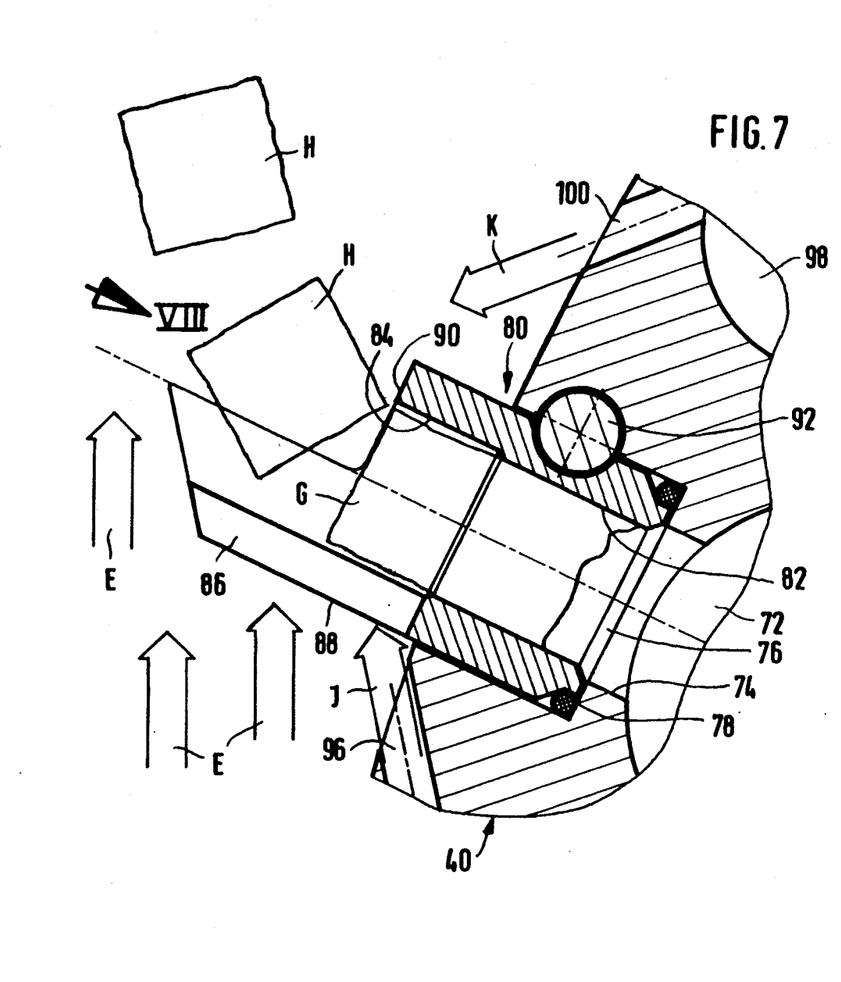
FIG. 7 is a much enlarged cutout of FIG. 5.
Figure 8:
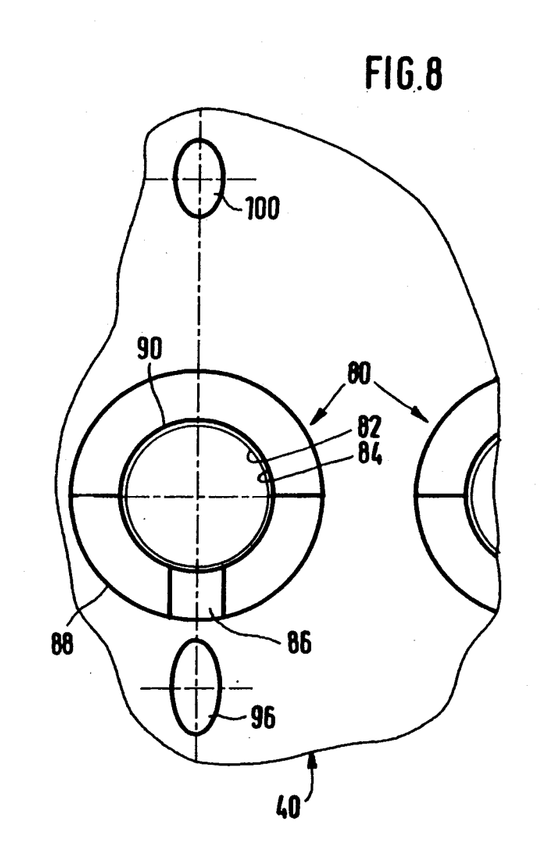
FIG. 8 is the view in the direction of arrow VIII in FIG. 7.
Figure 9:
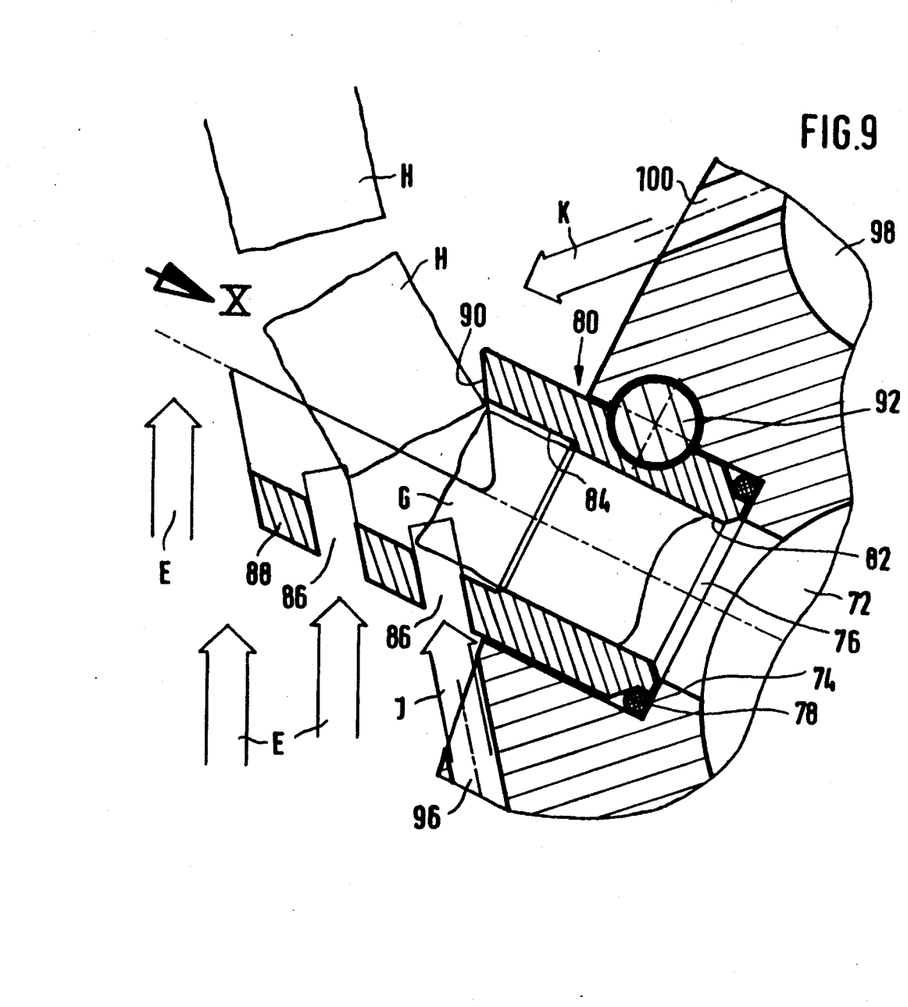
FIG. 9 is a cutout corresponding to FIG. 7, showing modified details.
Figure 10:
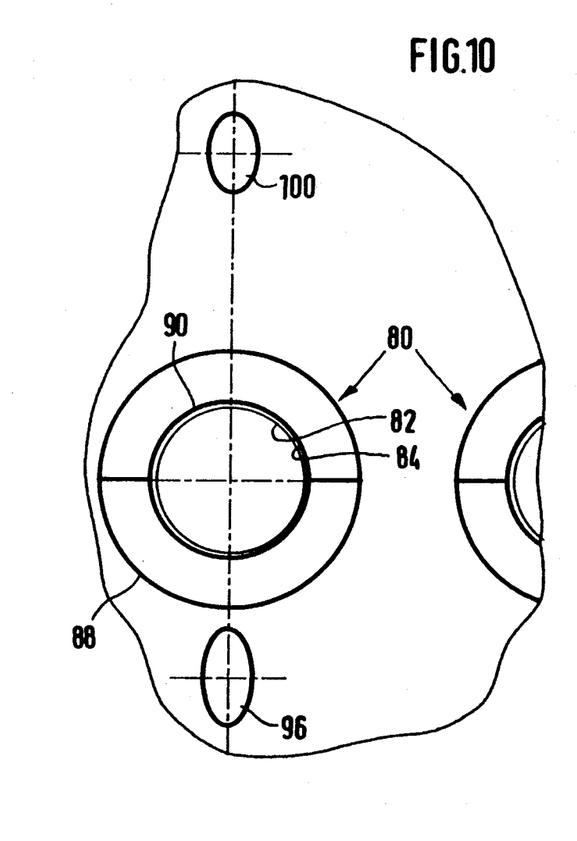
FIG. 10 the view in the direction of arrow X in FIG. 9.

Each of the extruder nozzles 80 of which one embodiment is shown in FIGS. 7 and 8 and another one in FIGS. 9 and 10 has an axially inner narrower portion 82 which determines the cross section of a strand G of the doughy mass produced in the extruder nozzle 80, and an axially outer enlarged portion 84 adapted to be vented from outside through at least one breakthrough 86 to promote the drying of the strand G. According to FIGS. 7 and 8, the breakthrough 86 is provided in the form of an axial slot positioned at the windward side of the extruder nozzle 80, with respect to the general flow of gas E, and extends from the beginning of the enlarged portion 84 up to the free end of the extruder nozzle 80.

In the case of the two embodiments of the extruder nozzle 80 shown in FIGS. 7 and 8, on the one hand, and in FIGS. 9 and 10, on the other hand, their half lying at the leeward side with respect to the general flow of gas E in the axially outer part of the widened portion 84 is removed, such as by milling, so that a semitubular shield 88 is what remains at the windward side, while a breakaway edge 90 is formed at the leeward side. According to FIGS. 7 and 8 this edge lies in a plane at right angles to the longitudinal axis of the extruder nozzle 80, according to FIGS. 9 and 10, on the other hand, it is disposed parallel to the oblique breakthroughs 86.

In each lance 40 there are two tie bolts 92, each extending at one side of the center plane A in longitudinal direction of the lance 40 and serving to lock the extruder nozzle 80 which is pressed into the respective half of the lance 40 against axial displacement and rotation.

Each lance 40 further comprises two lower pressure gas ducts 94 which extend parallel to its conveyor channel 60 and from which pressure gas nozzles 96 lead away such that per breakthrough 86 of each extruder nozzle 80 there is one pressure gas nozzle 96 directed towards it. The pressure gas ducts 94 are fed intermittently by way of electromagnetic valves of known design with compressed air which may be dried and preheated. The lower pressure gas nozzles 96 thus emit pressurized air in pulses toward the opening range of the associated extruder nozzle 80. In a sharply focussed jet J, the pressurized air acts pulsatingly on the strand G through the or a breakthrough in the respective extruder nozzle 80, whereby an extruded particle H breaks off from the strand at each blast of air. During the intervals between each two blasts of air a weaker pressurized air stream may issue from the pressure gas nozzles 96.

Another pressure gas duct 98, likewise in parallel with the conveyor channel 60, is arranged in the upper area of each lance 40. It is fed continuously and/or intermittently, alternating with the pressure gas ducts 94, with hot, dry pressurized air. Pressure gas nozzles 100 depart from the upper pressure gas duct 98 which are each directed from above at an acute angle against the opening range of an extruder nozzle 80. The extruded particle H forming in the same thus is dried also at the side which is the leeward side with respect to the general flow of gas E by a hot air jet K whose pressure prevents it from breaking off too soon, before its free end has reached the end of the shield 88.

The angle formed between each of the pressure gas nozzles 96 and 100 and the axial direction of the respective extruder nozzle 80 preferably is from about 30° to 50° so that the pressurized gas jets J and K issuing from the pressure gas nozzles 96 and 100 impart pulses of force to the strand G having a component in the direction of extrusion.

The extruder nozzles 80, for instance, are made of precious metal or plastics and are exchangeable for example against extruder nozzles with a narrow portion 82 having a greater or smaller diameter and/or with a longer or shorter shield 88. In this manner the diameter and length of the resulting extruded particles H may be varied, while it is possible to adapt the frequency of the pressurized air blasts supplied through the pressure gas nozzles 96 to the extrusion speed of the strand G and the desired length of the extruded particles H.

When severed, the extruded particles H are entrained in upward direction by the general flow of gas E. At the same time, a fluidized bed F or whirling bed is formed within the trough 53 defined by the semishells 52 and the guide vanes 42 and 44 and in it the extruded particles H are dried still further. When a given quantity of extruded particles H has formed in a treatment chamber 12 and the drying thereof has been completed, the corresponding gas inlet 16 is closed so that the fluidized bed F in the respective treatment chamber will collapse and the extruded particles H accumulate in the trough 53. Thereupon, the guide vanes 42 and 44 are swung into their emptying position so that the extruded particles H will trickle down as described and can be removed.

Figure 4:
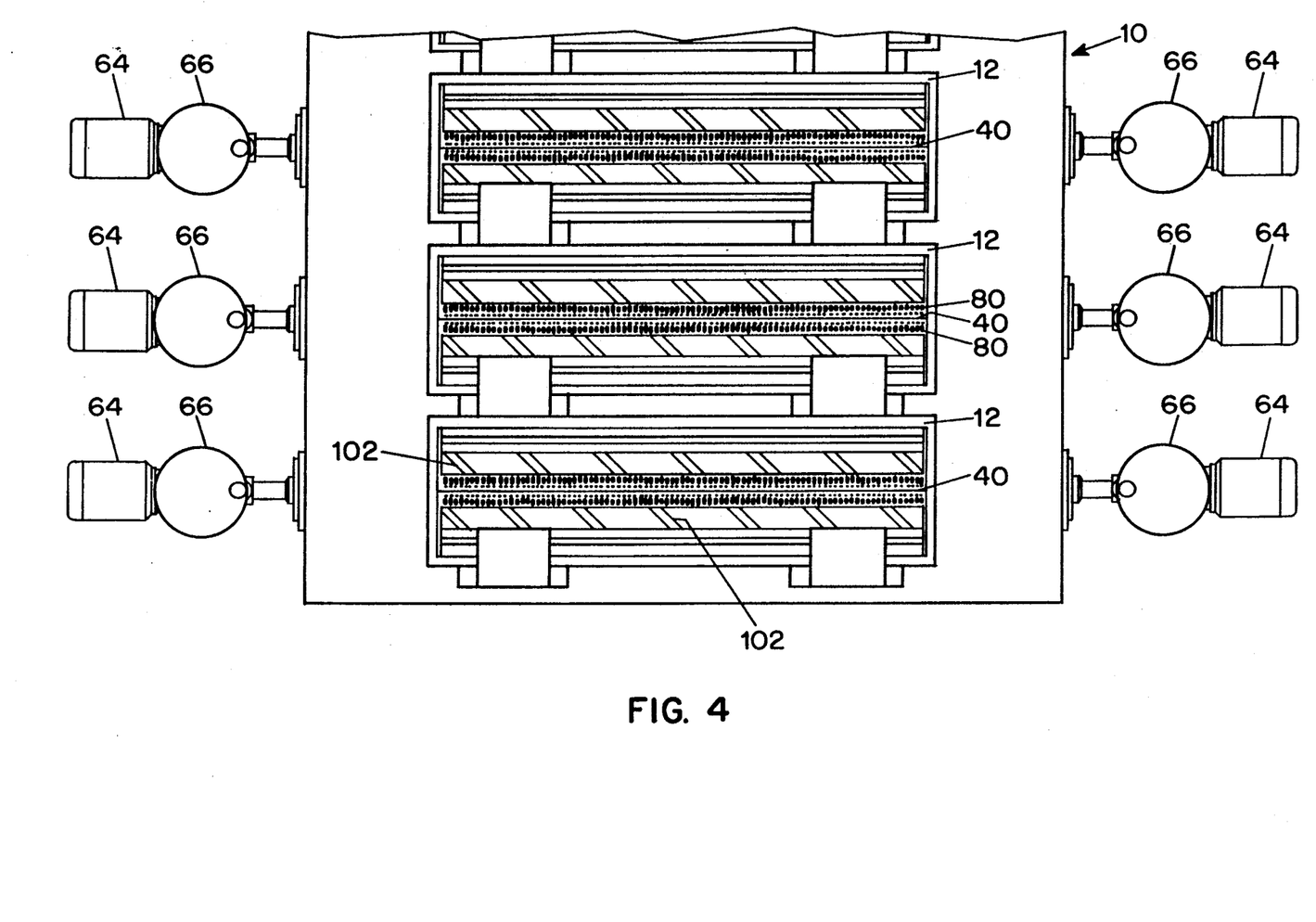
FIG. 4 is the top plan view in the direction of arrow IV in FIG. 1.

According to FIG. 4, the guide vanes 42 and 44 and/or the semishells 52 are formed with oblique corrugations or fins 102 having the same direction at both sides of the lance 40, when looked at from the top. Such fins 102 impart an oblique direction to the general flow of gas E so that the fluidized bed F at both sides of the lance 40 will travel in opposite directions along the lance, whereby the extruded particles H are mixed especially thoroughly.

When the lids 28 are swung open, the treatment chambers 12 offer ready access for cleaning. Nozzles 104 are associated with both the air supply chambers 20 and the spent air chambers 24 for cleaning liquid to be sprayed in.

What is claimed is:

1. A method of preparing extruded particles to avoid agglomeration with other extruded particles upon dropping comprising the steps of:

extruding a doughy mass in the form of a strand transversely into a first gas stream which is upwardly directed wherein said first gas stream upwardly directs said extruded particles to produce a fluidized bed of said particles; and drying and breaking said strand into particles using said first gas stream and a second gas stream which is upwardly directed and sharply focussed onto the surface of said strand.

2. The method according to claim 1 wherein said second gas stream is directed pulsatingly against said strand.

3. The method according to claim 2 wherein during the time in between the pulses, said second gas stream is directed onto the surface of said strand at a lower gas pressure than during the pulses.

4. The method according to claim 2 wherein a third gas stream is sharply focussed onto the opposite surface of said strand and is directed pulsatingly to said opposite surface in pulses alternate to said pulsating second gas stream.

5. The method according to anyone of claims 1, 2, 3, or 4 wherein said strand extruded transversely into said first gas stream is shielded for a limited distance on the surface contacted by said second gas stream and exposed on said opposite surface.

6. A method of preparing extruded particles comprising the steps of:

extruding a doughy mass in the form of a strand transversely into a first gas stream, and drying and breaking said strand into particles using said first gas stream, a second gas stream, and a third gas stream wherein said second gas stream is pulsatingly directed and sharply focussed onto the surface of said strand, and wherein said third gas stream is sharply focussed onto the opposite surface of said strand and is directed pulsatingly to said opposite surface in pulses alternate to said pulsating second gas stream.

* * * * *